US00PP12533P2

(12) United States Plant Patent
Vandenberg et al.

(10) Patent No.: US PP12,533 P2
(45) Date of Patent: Apr. 9, 2002

(54) CHRYSANTHEMUM PLANT NAMED 'YOBAY CITY'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,369

(22) Filed: Feb. 1, 2001

(51) Int. Cl.[7] ..... A01H 5/00
(52) U.S. Cl. ..... Plt./286

(58) Field of Search ..... Plt./286

*Primary Examiner*—Bruce R. Campell
*Assistant Examiner*—Anne Marie Grünberg
(74) *Attorney, Agent, or Firm*—C.A. Whealy

(57) ABSTRACT

A distinct cultivar of Chrysanthemum plant named 'Yobay City', characterized by its upright and uniformly mounded plant habit; dark green and glossy foliage; uniform flowering response; early flowering, eight-week response time; large daisy-type inflorescences that are about 7.9 cm in diameter; purple and white bi-colored ray florets and bright yellow disc florets; and excellent postproduction longevity with plants maintaining good substance and color for at least three weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'Yobay City'.

The new Chrysanthemum is a product of a planned breeding program conducted by the Inventors in Salinas, Calif. and Fort Myers, Fla. The objective of the breeding program is to create new potted Chrysanthemum cultivars that are suitable for year-round production with uniform plant growth habit, desirable inflorescence form and floret colors, fast response time, and excellent postproduction longevity.

The new Chrysanthemum originated from a cross made by the Inventors in May, 1993, in Salinas, Calif., of a proprietary Chrysanthemum seedling selection identified as code number YB-4168, not patented, as the female, or seed, parent with the Chrysanthemum cultivar Mobile, disclosed in U.S. Plant Pat. No. 9,335, as the male, or pollen, parent. The new Chrysanthemum was discovered and selected by the Inventors as a single flowering plant within the progeny of the stated cross grown in a controlled environment in Fort Myers, Fla. in November, 1996. The selection of this plant was based on its uniform plant growth habit, desirable inflorescence form and floret colors, fast response time,and excellent postproduction longevity. Plants of the new Chrysanthemum differ from plants of both parents primarily in ray floret coloration.

Asexual reproduction of the new Chrysanthemum by vegetative tip cuttings was first conducted in Fort Myers, Fla. in February, 1997. Asexual reproduction by cuttings has shown that the unique features of this new Chrysanthemum are stable and reproduced true to type in successive generations.

SUMMARY OF THE INVENTION

The cultivar Yobay City has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yobay City'. These characteristics in combination distinguish 'Yobay City' as a new and distinct Chrysanthemum:

1. Upright and uniformly mounded plant habit.
2. Dark green and glossy foliage.
3. Uniform flowering response.
4. Early flowering, eight-week response time.
5. Large daisy-type inflorescences that are about 7.9 cm in diameter.
6. Purple and white bi-colored ray florets and bright yellow disc florets.
7. Excellent postproduction longevity with plants maintaining good substance and color for at least three weeks in an interior environment.

Plants of the new Chrysanthemum can be compared to plants of the Chrysanthemum cultivar New Yoorleans, disclosed in U.S. Plant Pat. No. 11,215. In side-by-side comparisons conducted by the Inventors in Salinas, Calif., plants of the new Chrysanthemum differ from plants of the cultivar New Yoorleans in the following characteristics:

1. Plants of the new Chrysanthemum are more compact than plants of the cultivar New Yoorleans.
2. Plants of the new Chrysanthemum have a more uniform spray formation than plants of the cultivar New Yoorleans.
3. Under low light or high temperature conditions, ray floret color of the new Chrysanthemum retention is better than ray floret color retention of the cultivar New Yoorleans.

Plants of the new Chrysanthemum can be compared to plants of the Chrysanthemum cultivar Tijuana, disclosed in U.S. Plant Pat. No. 9,083. In side-by-side comparisons conducted by the Inventors in Salinas, Calif., plants of the new Chrysanthemum differ from plants of the cultivar Tijuana in the following characteristics:

1. Plants of the new Chrysanthemum are more compact and more outwardly spreading than plants of the cultivar Tijuana.
2. Plants of the new Chrysanthemum are stronger and sturdier than plants of the cultivar Tijuana.
3. Plants of the new Chrysanthemum have thicker, darker green and glossier foliage than plants of the cultivar Tijuana.
4. Ray floret color of the new Chrysanthemum is more blue purple than ray floret color of Tijuana.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Yobay City' grown a natural spray-type.

The photograph at the bottom of the sheet comprises a close-up view of typical inflorescences of 'Yobay City' grown as a natural spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the late autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as natural spray-types. Measurements and numerical values represent averages of typical flowering plants.

Botanical classification: *Chrysanthemum×morifolium* cultivar Yobay City.

Commercial classification: Daisy-type potted Chrysanthemum.

Parentage:

*Female, or seed, parent.*—Proprietary *Chrysanthemum×morifolium* seedling selection identified as code number YB-4168, not patented.

*Male, or pollen, parent.*—*Chrysanthemum×morifolium* cultivar Mobile, disclosed in U.S. Plant Pat. No. 9,335.

Propagation:

*Type.*—Terminal tip cuttings.

*Time to initiate roots.*—About four days at 21° C.

*Time to produce a rooted cutting.*—About ten days at 21° C.

*Root description.*—Fibrous and well-branched.

Plant description:

*Appearance.*—Herbaceous daisy-type potted Chrysanthemum typically grown as a natural spray-type. Stems upright and outwardly spreading giving a uniformly mounded appearance to the plant. Freely branching, about four lateral branches develop after removal of terminal apex (pinching); dense and full plants. Moderate vigor. Relatively compact.

*Plant height.*—About 23 cm.

*Plant width.*—About 39.5 cm.

*Lateral branches.*—Length: About 18 cm. Diameter: About 4 mm. Internode length: About 2.4 cm. Strength: Strong. Texture: Pubescent. Color: 146A.

*Foliage description.*—Arrangement: Alternate. Quantity of leaves per lateral stem: About 10. Length: About 7.4 cm. Width: About 6.6 cm. Apex: Cuspidate. Base: Mostly truncate to attenuate. Margin: Palmately lobed, sinuses between lateral lobes mostly divergent. Texture: Upper and lower surfaces with very fine pubescence; veins prominent on lower surface. Thick and leathery. Color: Young foliage, upper surface: Much darker than 147A; glossy. Young foliage, lower surface: 147A. Mature foliage, upper surface: Much darker than 147A; glossy. Mature foliage, lower surface: Darker than 147B. Venation, upper surface: 147A. Venation, lower surface: 147B. Petiole length: About 2 cm. Petiole diameter: About 3 mm. Petiole color: 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a natural spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for at least three weeks in an interior environment.

*Quantity of inflorescences.*—Freely flowering, about 5 inflorescences develop per lateral stem, or about 20 inflorescences per plant.

*Inflorescence bud.*—*Height: About* 6 mm. Diameter: About 8 mm. Color: Close to 143A.

*Inflorescence size.*—Diameter: About 7.9 cm. Depth (height): About 1.3 cm. Diameter of disc: About 1.9 cm. Receptacle diameter: About 7 mm.

*Ray florets.*—Shape: Elongated-oblong. Orientation: Initially upright, then about 65° from vertical. Aspect: Initially incurved, then mostly flat. Lenght: About 3.7 cm. Width: About 1.1 cm. Corolla tube length: About 1 mm. Apex: Emarginate. Base: Attenuate; very short corolla tube. Margin: Entire. Texture: Smooth, glabrous, satiny. Number of ray florets per inflorescence: About 22 arranged in one row. Color: When opening, upper and lower surfaces: Apex, mid-section and longitudinal stripes towards base, 77A; base and longtiudinal lines toward mid-section, 155D. Fully opened, upper surface: Apex, mid-section and longitudinal stripes towards base, 70A to 71A; base and longitudinal lines toward mid-section, 155D. Color does not fade with subsequent development. Fully opened, lower surface: Apex, mid-section and longitudinal stripes towards base, 155D underlain with 77A; base and longitudinal lines toward mid-section, 155D.

*Disc florets.*—Arrangement: Massed at center of receptacle. Shape: Tubular, elongated. Apex: Five-pointed. Length: About 6 mm. Width: Apex, about 2 mm; base, about 1 mm. Number of disc florets per inflorescence: About 155. Color: Immature: Close to 154A. Mature: Apex: 9A. Mid-section: 145D. Base: 155D.

*Peduncles.*—Length: First peduncle: About 4.9 cm. Fourth peduncle: About 7.1 cm. Diameter: About 2 mm. Angle to vertical: About 45° from vertical. Strength: Strong, flexible. Color: Close to 143A to 146A.

*Reproductive organs.*—Androecium: Present on disc florets only. Anther color: 12A. Pollen amount: None. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yobay City', as illustrated and described.

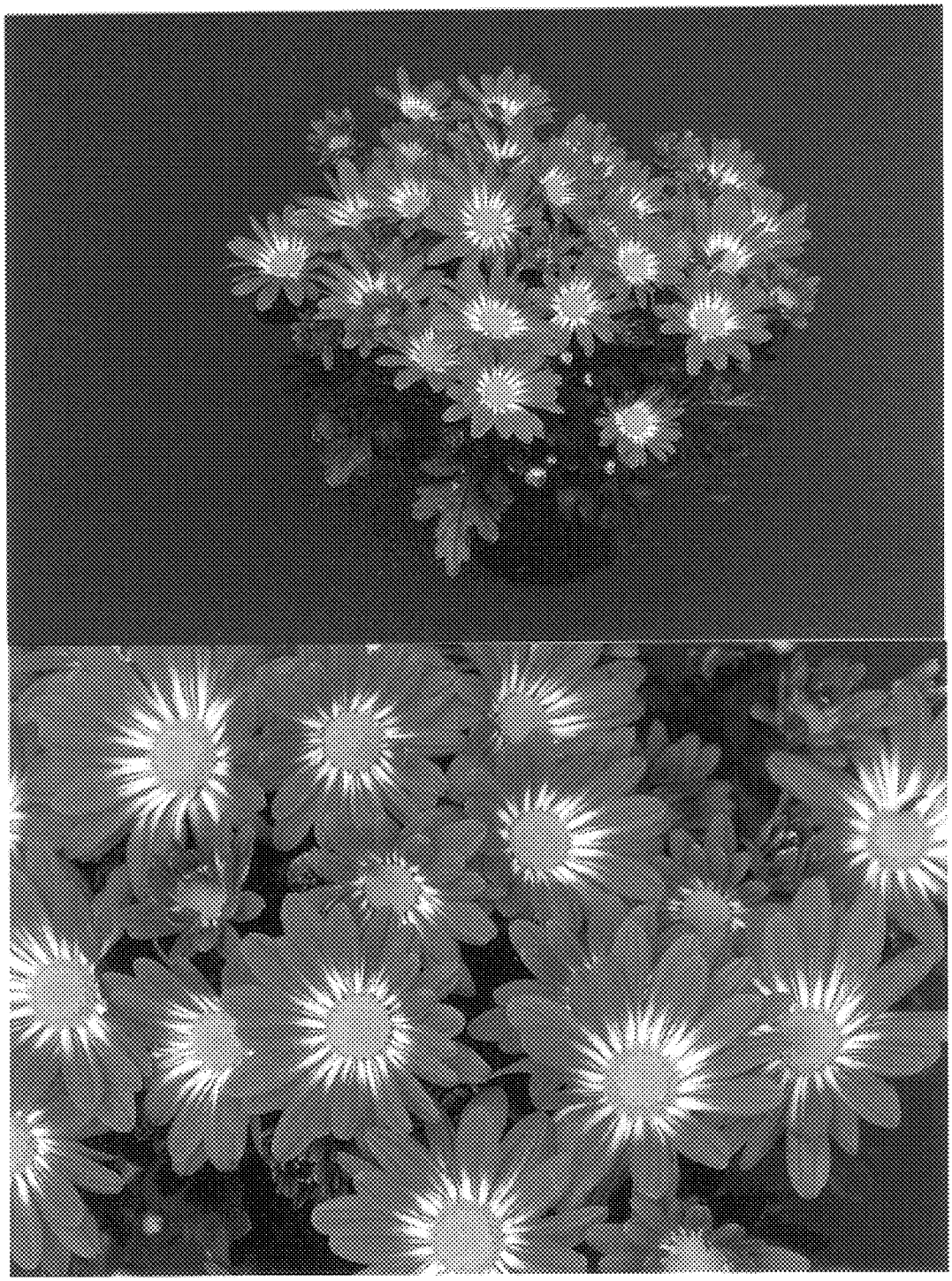

* * * * *